United States Patent
Anderson et al.

(12)

(10) Patent No.: US 6,423,518 B1
(45) Date of Patent: Jul. 23, 2002

(54) DESIGN AND PRODUCTION OF MUTANT 2, 5-DIKETO-D-GLUCONIC ACID REDUCTASE ENZYMES WITH ALTERED COFACTOR DEPENDENCY

(75) Inventors: Stephen Anderson, Princeton; Scott Banta, New Brunswick, both of NJ (US)

(73) Assignee: Rutgers, the State University, Brunswick, NJ (US)

( * ) Notice: Subject to any disclaimer, the term of this patent is extended or adjusted under 35 U.S.C. 154(b) by 0 days.

(21) Appl. No.: 09/658,645

(22) Filed: Sep. 11, 2000

(51) Int. Cl.⁷ .............................. C12N 9/02; C12N 9/04; C12Q 1/32; C12P 33/10; C07H 21/04
(52) U.S. Cl. .................. 435/189; 435/190; 435/26; 435/60.1; 536/23.2
(58) Field of Search ................. 435/189, 190, 435/69.1, 26; 536/23.2

(56) References Cited

U.S. PATENT DOCUMENTS

| 5,008,193 A | 4/1991 | Anderson et al. ............ 435/138 |
| 5,376,544 A | 12/1994 | Lazarus et al. ............. 435/190 |
| 5,583,025 A | 12/1996 | Lazarus et al. ............. 435/190 |
| 5,795,761 A | 8/1998 | Powers et al. .............. 435/190 |
| 5,912,161 A | 6/1999 | Lazarus et al. .......... 435/252.3 |

OTHER PUBLICATIONS

Rondeau et al, Novel NADPH–binding domain revealed by the crystal structure of aldolase reductase, Nature, 1992; 355;469–472.*

Wilson et al, An unlikely suger substrate site in the 1.65A structure of thr human aldose reductase holoenzyme implicated in diabetic complications, Science (1992); 257:81–84.*

Jez et al, Comparative anatomy of the aldo–ketoreductase superfamily, Biochem. (1997); 325:625–636.*

Khurana et al, Crystal structure of 2,5–diketo–gluconic acid reductase A complexed with NADPH at 2.1–A resolution, Proc. Natl. Acad. Sci. USA (1998); 95:6768–6773.*

* cited by examiner

*Primary Examiner*—Ponnathapu Achutamurthy
*Assistant Examiner*—Malgorzata Walicka
(74) *Attorney, Agent, or Firm*—Licata & Tyrrell P.C.

(57) ABSTRACT

Methods for producing mutant 2,5-diketo-D-gluconic acid reductase enzymes with altered cofactor dependency are provided. Also provided are mutant 2,5-diketo-D-gluconic acid reductase enzymes with altered cofactor dependency, DNA encoding these mutant enzymes, and vectors and host cells expressing these mutant enzymes.

5 Claims, 1 Drawing Sheet

SEQUENCE LISTING

```
<160> NUMBER OF SEQ ID NOS: 12

<210> SEQ ID NO 1
<211> LENGTH: 277
<212> TYPE: PRT
<213> ORGANISM: Corynebacterium sp.

<400> SEQUENCE: 1

Thr Val Pro Ser Ile Val Leu Asn Asp Gly Asn Ser Ile Pro Gln Leu
  1               5                  10                  15

Gly Tyr Gly Val Phe Lys Val Pro Pro Ala Asp Thr Gln Arg Ala Val
             20                  25                  30
```

Glu Glu Ala Leu Glu Val Gly Tyr Arg His Ile Asp Thr Ala Ala Ile
        35                  40                  45

Tyr Gly Asn Glu Glu Gly Val Gly Ala Ala Ile Ala Ala Ser Gly Ile
    50                  55                  60

Ala Arg Asp Asp Leu Phe Ile Thr Thr Lys Leu Trp Asn Asp Arg His
65                  70                  75                  80

Asp Gly Asp Glu Pro Ala Ala Ile Ala Glu Ser Leu Ala Lys Leu
                85                  90                  95

Ala Leu Asp Gln Val Asp Leu Tyr Leu Val His Trp Pro Thr Pro Ala
        100                 105                 110

Ala Asp Asn Tyr Val His Ala Trp Glu Lys Met Ile Glu Leu Arg Ala
        115                 120                 125

Ala Gly Leu Thr Arg Ser Ile Gly Val Ser Asn His Leu Val Pro His
        130                 135                 140

Leu Glu Arg Ile Val Ala Ala Thr Gly Val Val Pro Ala Val Asn Gln
145                 150                 155                 160

Ile Glu Leu His Pro Ala Tyr Gln Gln Arg Glu Ile Thr Asp Trp Ala
                165                 170                 175

Ala Ala His Asp Val Lys Ile Glu Ser Trp Gly Pro Leu Gly Gln Gly
        180                 185                 190

Lys Tyr Asp Leu Phe Gly Ala Glu Pro Val Thr Ala Ala Ala Ala
        195                 200                 205

His Gly Lys Thr Pro Ala Gln Ala Val Leu Arg Trp His Leu Gln Lys
        210                 215                 220

Gly Phe Val Val Phe Pro Lys Ser Val Arg Arg Glu Arg Leu Glu Glu
225                 230                 235                 240

Asn Leu Asp Val Phe Asp Phe Asp Leu Thr Asp Thr Glu Ile Ala Ala
                245                 250                 255

Ile Asp Ala Met Asp Pro Gly Asp Gly Ser Gly Arg Val Ser Ala His
            260                 265                 270

Pro Asp Glu Val Asp
        275

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 2
ccgcacctcg agcgcatc                                                 18

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 3

Pro His Leu Glu Arg Ile
 1               5

<210> SEQ ID NO 4
<211> LENGTH: 18
<212> TYPE: DNA
<213> ORGANISM: Artificial Sequence

```
<220> FEATURE:
<223> OTHER INFORMATION: Description of Artificial Sequence: Synthetic

<400> SEQUENCE: 4
ccgcacctcg aacgcatc                                                    18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 5
gagcgcctcg aagagaac                                                    18

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic

<400> SEQUENCE: 6

Glu Arg Leu Glu Glu Asn
  1               5

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 7
gagcgcctcg aggagaac                                                    18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 8
caggccgtgc tccgttggca c                                                21

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 9

Gln Ala Val Leu Arg Trp His
  1               5

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 10
```

```
caggccgtcc tcaggtggca c                                         21

<210> SEQ ID NO 11
<211> LENGTH: 9
<212> TYPE: PRT
<213> ORGANISM: Corynebacterium sp.

<400> SEQUENCE: 11

Phe Pro Lys Ser Val Arg Arg Glu Arg
 1               5

<210> SEQ ID NO 12
<211> LENGTH: 9
<212> TYPE: PRT
<213> ORGANISM: Corynebacterium sp.

<400> SEQUENCE: 12

Ile Pro Lys Ser Ala Asp Pro Asp Arg
 1               5
```

US 6,423,518 B1

DESIGN AND PRODUCTION OF MUTANT 2, 5-DIKETO-D-GLUCONIC ACID REDUCTASE ENZYMES WITH ALTERED COFACTOR DEPENDENCY

FIELD OF THE INVENTION

The present invention relates to methods for designing 2,5-diketo-D-gluconic acid reductase enzymes with altered NADPH and NADH cofactor dependency by site-directed mutagenesis of one or more amino acids in the cofactor specificity site of the 2,5-diketo-D-gluconic acid reductase enzyme. The present invention also relates to mutated forms of the enzyme having altered NADPH and NADH cofactor dependency, DNA encoding these mutant enzymes, and vectors and host cells expressing these mutant enzymes. Mutated forms of the present invention exhibit non-wild type enzymatic activity with NADH, non-wild type activity with NADPH, activity with both NADPH and NADH, and altered expression characteristics.

BACKGROUND OF THE INVENTION

L-ascorbic acid, also known as vitamin C, is an essential part of the diet and an important antioxidant. Increasing health consciousness of the public and use of this product in preservation of food has led to an increased demand for vitamin C. It is estimated that world-wide consumption of this specialty chemical exceeds 50,000 tons/year.

Vitamin C is industrially produced by the modified Reichstein and Grussner synthesis which requires one fermentation step by *Acetobacter suboxydans* and five chemical steps. A dual fermentation system has also been described wherein D-glucose is converted to 2,5-diketo-D-gluconic acid by *Erwinia herbicola*. The 2,5-diketo-D-gluconic acid is then converted to 2-keto-L-gulonic acid, a direct precursor of L-ascorbic acid, by Corynebacterium sp. (Sonoyama et al. App. Environ. Microbiol. 1982 43:1064–1069). This precursor is converted to ascorbic acid through acid or base catalyzed cyclization. Since this intermediate has greater shelf stability and shelf life than ascorbic acid, it is more practical to stockpile 2-keto-L-gulonic acid for subsequent conversion to vitamin C.

Production of 2-keto-L-gulonic acid from D-glucose via a single fermentation step has been described by Anderson et al. (Science 1985 230:144–149). In this process, 2,5-diketo-D-gluconic acid reductase (2,5-diketo-D-gluconic acid reductase A, also known as 2,5-diketo-D-gluconic acid reductase II) was cloned from Corynebacterium sp. and expressed in *Erwinia herbicola*. The resulting metabolically-engineered organism can produce 2-keto-L-gulonic acid from D-glucose in a single fermentation step.

A method for producing 2-keto-L-gulonic acid from glucose in vitro was also recently described (Boston et al. Biotrans. 1999: 4th International Symposium on Biocatalysis and Biotransformation).

While high yields of 2-keto-L-gulonic acid are obtained with Corynebacterium sp. 2,5-diketo-D-gluconic acid reductase, the compound 2,5-diketo-D-gluconic acid is actually a poor substrate for this enzyme. Accordingly, various attempts have been made to improve the catalytic efficiency, thermal stability and/or expression levels of 2,5-diketo-D-gluconic acid reductase in this single fermentation process.

U.S. Pat. Nos. 5,376,544, 5,583,025, 5,912,161 and 5,795,761 disclose mutants of 2,5-diketo-D-gluconic acid reductase A with increased catalytic activity, increased expression levels, and/or enhanced temperature stability. Mutants disclosed in U.S. Pat. Nos. 5,376,544, 5,583,025, and 5,912,161 include replacement or deletion of the amino acid residue at position 2, 5, 7, 55, 57, 165, 166, 167, 168, 187, 188, 189, 190, 191, 192, 193, 194, 195, 196, 197, 198, 224, 225, 226, 227, 228, 229, 230, 231, 232, 233, 234, 262, 263, 264, 265, 266, 267, 268, 269, 270, 271, 272, 273, 274, 275, 276, 277 or 278 of wild type 2,5-diketo-D-gluconic acid reductase A. Mutants disclosed in U.S. Pat. No. 5,795,761 include replacement or deletion of the amino acid residue at position 21, 22, 23, 24, 25, 46, 47, 48, 49, 50, 51, 52, 164, 169, 170, 199, 200 or 235 of wild type 2,5-diketo-D-gluconic acid reductase A.

The 2,5-diketo-D-gluconic acid reductase enzyme exhibits a dramatic preference for NADPH over NADH. When the available concentration of NADPH is low, then overall activity of the enzyme is limited. However, increasing the available concentration of NADPH in the cell can be difficult and increasing the amount added to an in vitro reaction can be quite expensive as NADPH is a costly component.

The crystal structure of wild type 2,5-diketo-D-gluconic acid reductase A with bound NADPH has been disclosed (Khurana et al. Proc. Natl Acad. Sci. 1998 95:6768–6773). Sequence alignment with the NADPH cofactor binding loop of similar enzymes such as aldose reductase has also been performed (Rondeau et al. Nature 1992 355:469; Wilson et al. Science 1992 257:81; Jez et al. Biochem. J. 1997 326:625–636). Accordingly, some of the residues of this enzyme that interact with the NADPH molecule have been delineated.

A poster was presented by Banta et al. on Nov. 16, 1998 at the Annual Meeting of the American Institute of Chemical Engineers suggesting improving the NADPH kinetics of the enzyme as a means for improving the overall catalysis. However, no means for achieving this were described. Nor was there any mention of improving NADH kinetics.

SUMMARY OF THE INVENTION

An object of the present invention is to provide a method of producing mutant 2,5-diketo-D-gluconic acid reductase enzymes with altered cofactor dependency, which comprises identifying a cofactor specificity site in the enzyme and mutating an amino acid in the identified cofactor specificity site of wild type 2,5-diketo-D-gluconic acid reductase.

Another object of the present invention is to provide mutant 2,5-diketo-D-gluconic acid reductase enzymes with altered cofactor dependency, DNA encoding these mutant enzymes, and vectors and host cells expressing these mutant enzymes.

DETAILED DESCRIPTION OF THE INVENTION

Figure 1:
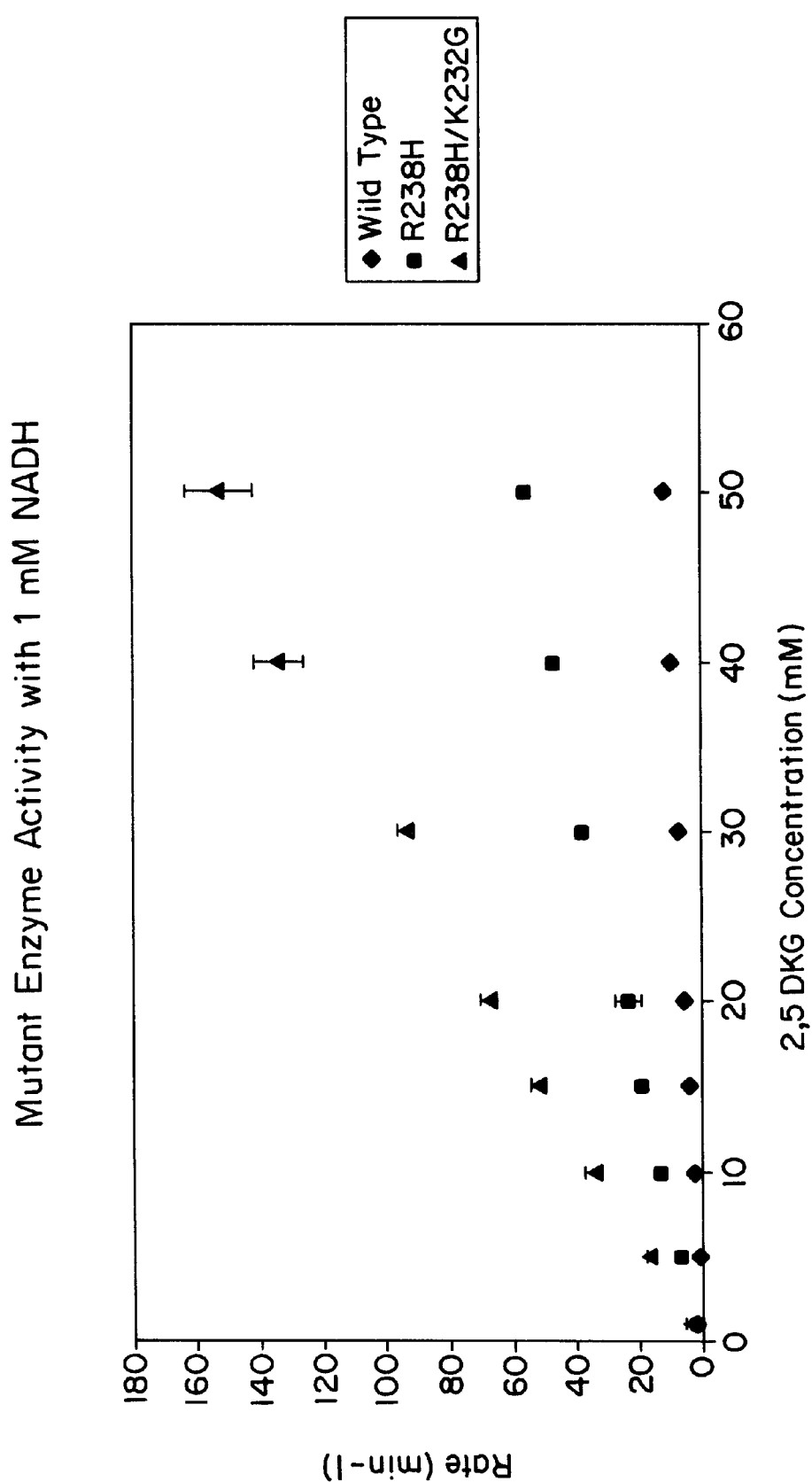
FIG. 1 provides a graph showing the enzymatic activity of wild type 2,5-diketo-D-gluconic acid reductase A versus two mutants of this enzyme in the presence of 1 mM NADH and varying concentrations of the substrate, 2,5-diketo-D-gluconic acid. Wild type enzyme is depicted by filled diamonds. Mutant enzyme R238H is depicted by filled squares. A double mutant enzyme R238H/K232G is depicted by filled triangles.

There are at least two known enzymes that catalyze the conversion of 2,5-diketo-D-gluconic acid to 2-keto-L-gulonic acid, an immediate precursor to ascorbic acid or vitamin C. These are 2,5-diketo-D-gluconic acid reductases A and B. Through use of sequence alignment, the 2,5-diketo-D-gluconic acid reductases have been identified as members of the aldo-keto reductase superfamily, whose members include aldose reductases, aldehyde reductases, hydroxysteroid dehydrogenases and dihydrodiol dehydrogenases, to name a few (Jez et al. Biochem. J. 1997 326:625–636).

Both 2,5-diketo-D-gluconic acid reductases A and B prefer NADPH as a cofactor. In a typical cell, the concentration of NADP(H) is about 3 to 5 times less than NAD(H). In addition, NADPH can cost an order of magnitude more than NADH. Accordingly, the present invention provides methods for producing mutant enzymes that catalyze the conversion of 2,5-diketo-D-gluconic acid to 2-keto-L-gulonic acid by use of the cofactor NADH, altered concentrations of NADPH, or a combination of NADH and NADPH.

For purposes of this invention, by "mutant" it is meant not only an enzyme with amino acid substitutions as compared to the wild type sequence, but also an enzyme comprising additional inserted amino acids as well as deletions of amino acids as compared to the wild type sequence.

A cofactor specificity site in the NADPH-dependent wild type 2,5-diketo-D-gluconic acid reductase A enzyme (ATCC Strain No. 31090; Genbank Accession No. 4699594; SEQ ID NO:1) has been identified. By "cofactor specificity site" it is meant the amino acid residues of the enzyme which interact directly or indirectly with the bound NADPH cofactor. More specifically, for purposes of the present invention, by cofactor specificity site it is meant those residues that interact directly or indirectly with the 2' phosphate on the adenosine moiety of NADPH. These residues are believed to be responsible for the marked preference of this enzyme for NADPH over NADH. Residues in the cofactor specificity site, or more specifically 2' phosphate interacting residues, including K232, S233, V234, R235 and R238 of wild type 2,5-diketo-D-gluconic acid reductase A, were identified by homology to the three-dimensional structure of aldose reductase (Rondeau et al. Nature 1992 355:469; Wilson et al. Science 1992 257:81) and 2,5-diketo-D-gluconic acid reductase A (Khurana et al. Proc. Natl Acad. Sci. 1998 95:6768–6773) using two computer programs, the Ligand-Protein Contacts program and the Contacts of Structural Units program (Sobolev et al. Bioinformatics 1999 15:327–332).

The first residue, K232, lies underneath the bound cofactor and makes several contacts with the NADPH molecule. The backbone amide nitrogen forms a hydrogen bond with the adenosine side phosphate of the pyrophosphate group. The aliphatic carbon atoms of the side chain line lie beneath the adenosine ribose. Further, the positively charged nitrogen of the $\epsilon$ NH$_2$ group forms an ionic bond with the 2' phosphate of NADPH and a hydrogen bond with the adenosine ribose. This residue is highly conserved in members of the aldo-keto reductase superfamily. A notable exception to this conservation is found in the 3α-hydroxysteroid dehydrogenase (3α-HSD) enzyme, which exhibits NADH activity and has an arginine at this site (Jez et al. Biochem. J. 1997 326:625–636). Mutation of this lysine residue in other aldo-keto reductase enzymes such as aldose reductase and aldehyde reductase to methionine resulted in increases in $K_M$ for both substrate and cofactor (NADPH) for both enzymes (Bohren et al. J. Biol. Chem. 1991 266:24031–24037). Similar results were obtained by mutating the same lysine in human aldose reductase to glutamate; however, a reduction in the $K_M$ for the substrate was observed when arginine was substituted for this lysine in the aldose reductase enzyme (Yamaoka et al. Biochem. Biophys. Res. Comm. 1992 183:327–333). The cofactor specificity of these aldose reductase mutants was not examined in these experiments.

The next residue that interacts with the 2' phosphate is the very highly conserved serine at position 233. This residue lies adjacent to Lys232 and is buried beneath the bound cofactor. There is a hydrogen bond between the side chain hydroxyl and the 2' phosphate group. In addition, the α and β carbons and the backbone carbon and oxygen exhibit close Van der Waals interactions with the adenosine ribose.

The arginine at position 238 is also highly conserved. This residue appears to be very important for proper cofactor binding. One of the terminal guanido nitrogens is located in a position for ionic binding with the 2' phosphate. In addition, both terminal nitrogens can form hydrogen bonds with nitrogens in the adenine ring. The carbon chain of the residue lies next to the adenine ring and a stacking interaction is observed. Another hydrogen bond between the $\epsilon$ nitrogen and a nitrogen in the adenine ring is also observed. Thus, it is believed that Arg238 is very important for aligning the position of the adenine ring. Further, the positive charge of the nitrogens favors NADPH as a cofactor. For these reasons, this arginine has been studied in other members of the aldo-keto reductase superfamily. Mutation of this arginine to methionine in human aldose reductase was shown to greatly increase the $K_M$ for NADPH, but only slightly increase the $K_M$ for NADH, the $K_m$ for substrate, and the overall $k_{cat}$ (Kubisecki, T. J. and Flynn, T. G. J. Biol. Chem. 1995 270:16911–16917). The same mutation in 3α-HSD, which uses both NADH and NADPH for catalysis, dramatically increased the $K_M$ for both NADPH and NADH, but had only a minor effect on the other steady state parameters (Ratnam et al. Biochem. 1999 38:7856–7864). Thus, since this residue appears to only affect cofactor interactions, it is believed to be a particularly useful target for mutagenesis.

Val234 is less conserved in the aldo-keto reductase superfamily. For example, in other members of the superfamily position 234 is an isoleucine, threonine, serine, phenylalanine or tyrosine (Jez et al. Biochem. J. 1997 326:625–636). Val234 lies adjacent to Ser233, but is much more solvent accessible. Its backbone amide makes a hydrogen bond with the 2' phosphate. One of the γ carbons lies very close to the 2' phosphate, a proximity which may be exploited.

The arginine at position 235 was also implicated in cofactor specificity using coordinated from the available crystal structure for 2,5-diketo-D-gluconic acid reductase A (Khurana et al. Proc. Natl Acad. Sci. 1998 95:6768–6773) and the Ligand-Protein Contacts program and the Contacts of Structural Units program (Sobolev et al. Bioinformatics 1999 15:327–332). However, its role in cofactor binding has not been described. This residue is not well-conserved in the aldo-keto reductase superfamily. In fact, 2,5-diketo-D-gluconic acid reductase A is the only known member of this superfamily to contain arginine at this site. Other members have a threonine, asparagine, aspartate, lysine or histidine at position 235. Arg235 lies adjacent to Arg238, and the two residues together look like fingers cradling the 2' phosphate of NADPH. Its $\epsilon$ nitrogen and one of its terminal guanido nitrogens form a hydrogen bond and an ionic bond with the 2' phosphate, respectively. Val234 is found on the other side of this residue. Like Val234, Arg235 is fairly solvent accessible and its interactions with the rest of the cofactor are fairly minimal.

It is believed that other residues between or adjacent to the region of K232 through R238 may also have secondary interactions that are involved in promoting NADPH specificity. Thus, for example, mutations at residues 230, 231, 236 and 237 may also affect cofactor specificity. Accordingly, by "cofactor specificity site" it is also meant to include these residues.

The cofactor specificity site or sites in other 2,5-diketo-D-gluconic acid reductase enzymes can also be identified via sequence alignment with the reductase A enzyme. For example, the sequence alignment for the A and B (SEQ ID form ((SEQ ID NO:11 and 12, respectively) of the enzyme is as follows:

|        | 230 | 231 | 232 | 233 | 234 | 235 | 236 | 237 | 238 |
|--------|-----|-----|-----|-----|-----|-----|-----|-----|-----|
| A form | F   | P   | K   | S   | V   | R   | R   | E   | R   |
| B form | I   | P   | K   | S   | A   | D   | P   | D   | R   |

Thus, amino acids 231, 232, 233 and 238 of 2,5-diketo-D-gluconic acid reductase A and B are identical (Jez et al. Biochem. J. 1997326:625–636). Accordingly, it is believed that a cofactor specificity site comprising at least amino acids 231, 232, 233 and 238 exists in 2,5-diketo-D-gluconic acid reductase B as well.

Methods for the construction of plasmid ptrpl-35 containing the clone for the wild type enzyme are described in detail in U.S. Pat. No. 5,008,193.

Modifications to one or more amino acids in the identified cofactor specificity site can be made via site-directed mutagenesis. Various methods for site-directed mutagenesis are well known in the art. For example, a preferred procedure for site-directed mutagenesis, wherein one or a few base pairs are altered, can be performed by cloning the DNA sequence encoding the wild type enzyme into a recombinant plasmid containing an origin of replication derived from a single-stranded bacteriophage. An appropriate primer is then used to convert one or more nucleotides at an identified position or positions so that one or more amino acid residues in the cofactor specificity site are altered to different amino acid(s) or inserted or deleted.

Mutants can also be produced through PCR mutagenesis in accordance with well known methods such as described by Ho et al. (Gene 1989 77:51–59). In this method, four DNA primers are used during 2 PCR steps to produce the proper DNA cassette.

In a preferred method of cassette mutagenesis, an expression vector such as pATP003 is used. The pATP003 vector contains a GroES fragment fused to the N-terminus of the enzyme, which allows for high levels of expression in $E.\ coli$. The vector is also controlled by the lac promoter operator system, and is induced with the addition of IPTG. In a preferred embodiment, the $E.\ coli$ strain JM109 is used for expression. In this method, restriction sites that flank the 2' phosphate binding residues are used to doubly digest away a small DNA segment. The desired single-stranded mutagenic oligonucleotides are purchased and annealed together to produce a replacement DNA cassette. The new cassette is ligated into the vector, and the cassette is designed to eliminate a naturally occurring internal restriction site (PstI). The new vectors are transformed into $E.\ coli$, and colonies are grown up to 5 ml cultures. A plasmid extract kit is used to retrieve the mutant DNA, and they are screened for the missing PstI site. Positive mutants are then sequenced to verify the proper mutations.

Restriction sites that flank the region of interest do not naturally occur in the 2,5-diketo-D-gluconic acid reductase A gene, and thus were engineered into the gene for these experiments. A unique Bsu36 I was engineered upstream of the region of interest with three silent mutations. An Xho I site was also introduced immediately downstream of the region of interest. Another Xho I site that already existed in the reductase gene was then eliminated through a single silent mutation. This vector is referred to herein as pATP003.xb. By introducing these restriction sites into the pATP003 vector, it is possible to remove a 57 base pair cassette from the pATP003.xb vector with a double digestion of Bsu36 and Xho I. More specific details of the new restriction sites used in cassette mutagenesis are provided in Example 1.

The resulting double-stranded DNA is transformed into a host bacterium. Cultures of the transformed bacteria are plated on LB agar plates containing ampicillin, permitting colony formation from single cells that harbor the plasmid. The formed colonies were used to inoculate 5 ml mini-prep cultures in LB plus ampicillin. Plasmid DNA was prepared from these and was screened by DNA sequencing across the cassette region. Subsequent site-directed mutagenesis may be used to alter additional nucleotides in any mutant. Alternatively, mutants with more than one altered nucleotide can be constructed via well known techniques such as isolating restriction fragments and ligating the fragments into an expression vector.

The general strategy followed in making the mutations was to eliminate any strong interactions that favor the binding of the 2' phosphate of NADPH and replace these with residues that promote NADH binding. For example, both of the arginine residues and the lysine residues are positively charged and therefore attract the negative charge of the 2' phosphate. When these are replaced by polar uncharged residues, a hydrogen bond may be formed but the charge preference is removed. When these residues are replaced by negatively charged side chains, they may repel NADPH, thereby leaving the site open for NADH binding. Mutations with bulkier residues that may be able to fill in some of the space that is vacated by the absence of the phosphate in NADH have also been prepared. Mutations are screened in a native gel assay as described in Example 2.

In addition, there are several enzymes in the aldo-keto reductase superfamily of enzymes that use NADH as a cofactor. Single mutants have been prepared based on residues found at analogous positions of these other members of aldo-keto reductase superfamily enzymes. Further, chimeric enzymes that contain all of the same 2' phosphate binding residues as are found in the homologous enzymes have been made. For example, rat 3α-HSD can utilize both NADH and NADPH as cofactors, although it has a KM for NADH that is 57-fold higher than that for NADPH. The cofactor specificity residues for this aldo-keto reductase enzyme are different from 2,5-diketo-D-gluconic acid in three locations (Jez et al. Biochem. J. 1997 326:625–636). Accordingly, a triple mutant K232R/V234F/R235N can be produced and evaluated on an activity stained native gel. Other mutations can also be introduced into the same oligonucleotide cassette. For example, the R238H single mutant which promotes NADH activity can also be combined to form a quadruple mutant K232R/V234F/R235N/R238H. There are also several yeast reductases that can utilize NADH as a cofactor. For example, xylose reductase from Pachysolen tannophilus, which has three residues that are different from the 2,5-diketo-D-gluconic acid reductase binding site, can utilize NADH (Bolen et al. Yeast 1996 13:1367–1375). Accordingly, mutants containing one or more of these sites, such as a triple mutant V234T/R235F/R238T, which contains these three different residues, can also be prepared.

6'-deoxychalcone synthase isolated from soybeans has been shown to have NAD(P)H dependent activity (Welle et al. Euro. J. Biochem. 1991 196:423–430). Thus, the binding pocket of this enzyme can also be grafted into the reductase with the double mutant V234Y/R235D. A triple mutant further comprising R238H can also be prepared and tested. A hemolymph 3-dehydroecdysone 3β-reductase from Spodoptera littoralis (the cotton leafworm) has also been isolated and shown to have a $K_M$ of 22.8 μM for NADH (Chen et al. Eur. J. Biochem. 1996 242:394–401). Thus, the binding pocket of this enzyme can be grafted into 2,5-diketo-D-gluconic acid reductase to produce the double mutant S233T/R235S.

The focus of the mutagenesis effort was to identify the best kinetic profile with NADH, regardless of what this did to NADPH specificity. The primary goal was to identify mutations that improve the overall performance of the 2,5-diketo-D-gluconic acid reductase enzyme for use in a metabolically engineered cell or for use in an in vitro bioreactor.

Site-directed mutagenesis of one or more selected amino acids in the identified cofactor specificity site was demonstrated to result in mutant enzymes exhibiting increased activity with NADH, non-wild type activity with NADPH, and activity with both NADPH and NADH. Multiple single mutants were produced in the identified cofactor specificity site and screened for NADH and NADPH activity using a native gel assay as described in Example 2. Single mutants that exhibited NADH activity were then combined to produce various double and triple mutants. These double and triple mutants were also screened for NADH activity. Results from these assays are shown in Tables 1, 2 and 3. Also depicted in the tables are several examples of chimeric mutants comprising binding pockets of other enzymes in this superfamily with some specificity for NADH.

The data shown in Tables 1, 2 and 3 are the raw data from the native gel assay performed as described in Example 2. To derive these data, dark bands of the gel with each cofactor were first observed and the intensity of the band was documented on a scale of 0 to 3 stars. The gels were then stained to assess the amount of protein at the active band. This amount was also assigned a value of 0 to 3 stars. The activity columns of Tables 1, 2 and 3 have not been corrected to take into consideration the amount of protein. Thus, a mutant with 3 stars in NADPH activity and only 2 stars in amount of protein presumably has higher specific activity than a mutant with 3 stars in NADPH activity as well as 3 stars in protein amount.

TABLE 1

Mutations of main cofactor binding site residues

| Mutant | K 232 | S 233 | V 234 | R 235 | R 238 | Amount of Protein in Active Band | NADPH Activity | NADH Activity |
|---|---|---|---|---|---|---|---|---|
| wild type | | | | | | ** | *** | |
| K232G | G | | | | | *** | ** | * |
| K232H | H | | | | | *** | ** | |
| K232M | M | | | | | *** | ** | * |
| K232Q | Q | | | | | *** | *** | * |
| K232R | R | | | | | ** | ** | |
| K232S | S | | | | | *** | *** | * |
| K232T | T | | | | | *** | *** | |
| S233E | | E | | | | ** | | |
| S233K | | K | | | | * | | |
| S233M | | M | | | | * | | |
| S233N | | N | | | | * | | |
| S233T | | T | | | | * | *** | |
| S233V | | V | | | | * | | |
| V234D | | | D | | | *** | *** | |
| V234E | | | E | | | ** | *** | |
| V234I | | | I | | | * | *** | |
| V234M | | | M | | | * | *** | |
| V234N | | | N | | | * | *** | |
| V234Q | | | Q | | | * | *** | |
| V234S | | | S | | | * | ** | |
| V234M/R235C | | | M | C | | *** | *** | |
| R235C | | | | C | | *** | *** | |
| R235D | | | | D | | *** | ** | |
| R235E | | | | E | | *** | ** | |
| R235G | | | | G | | *** | ** | * |
| R235H | | | | H | | ** | *** | |
| R235M | | | | M | | ** | *** | |
| R235N | | | | N | | *** | *** | |
| R235Q | | | | Q | | ** | *** | |
| R235S | | | | S | | *** | *** | |
| R235T | | | | T | | *** | *** | * |
| R235Y | | | | Y | | ** | * | |
| R238D | | | | | D | ** | | |
| R238E | | | | | E | ** | | * |
| R238F | | | | | F | ** | *** | |
| R238G | | | | | G | ** | ** | |
| R238H | | | | | H | *** | *** | * |
| R238N | | | | | N | ** | ** | |
| R238Q | | | | | Q | *** | ** | |
| R238Y | | | | | Y | ** | *** | |

TABLE 1-continued

Mutations of main cofactor binding site residues

| Mutant | K 232 | S 233 | V 234 | R 235 | R 238 | Amount of Protein in Active Band | NADPH Activity | NADH Activity |
|---|---|---|---|---|---|---|---|---|
| K232G/R235G | G | | | G | | *** | | * |
| K232G/R235T | G | | | T | | *** | * | * |
| K232G/R238E | G | | | | E | *** | * | * |
| K232G/R238H | G | | | | H | *** | *** | ** |
| K232S/R235G | S | | | G | | *** | * | * |
| K232S/R235T | S | | | T | | *** | * | * |
| K232S/R238E | S | | | | E | *** | | * |
| K232S/R238H | S | | | | H | *** | *** | * |
| R235G/R238E | | | | G | E | *** | | * |
| R235G/R238H | | | | G | H | *** | *** | * |
| R235T/R238E | | | | T | E | *** | * | * |
| R235T/R238H | | | | T | H | *** | *** | * |
| K232G/R235G/R238E | G | | | G | E | *** | | * |
| K232G/R235T/R238E | G | | | T | E | *** | | * |
| K232G/R235G/R238H | G | | | G | H | *** | ** | * |
| K232G/R235T/R238H | G | | | T | H | *** | *** | * |
| K232S/R235G/R238E | S | | | G | E | *** | | * |
| K232S/R235T/R238E | S | | | T | E | *** | * | * |
| K232S/R235G/R238H | S | | | G | H | *** | | * |
| K232S/R235T/R238H | S | | | T | H | *** | ** | * |
| K232R/V234F/R235N | R | | F | N | | *** | * | |
| K232R/V234F/R235N/R238H | R | | F | N | H | *** | ** | * |
| V234Y/R235D | | | Y | D | | *** | * | |
| V234Y/R235D/R238H | | | Y | D | H | *** | * | |
| S233T/R235S | | T | | S | | *** | *** | * |
| S233T/R235S/R238H | | T | | S | H | *** | *** | * |
| V234T/R235F/R238T | | | T | F | T | *** | * | |
| V234T/R235F | | | T | F | | ** | ** | |

Additional mutants were also prepared with changes at residues F22 and A272. The double mutant F22Y/A272G has been disclosed previously to exhibit improved ability to convert 2,5-diketo-D-gluconic acid into 2-keto-L-gulonic acid. See U.S. Pat. No. 5,795,761. Table 2 shows results from native gel assays with these mutants.

TABLE 2

F22Y/A272G Mutants

| Mutant | F22 | K 232 | S 233 | R 235 | R 238 | A 272 | Amount of Protein in Active Band | NADPH Activity | NADH Activity |
|---|---|---|---|---|---|---|---|---|---|
| F22Y/A272G | Y | | | | | G | ** | *** | |
| F22Y/S233T/A272G | Y | | T | | | G | *** | *** | |
| F22Y/R235C/A272G | Y | | | C | | G | *** | *** | |
| F22Y/R238H/A272G | Y | | | | H | G | NYD | NYD | NYD |
| F22Y/K232G/R238E/A272G | Y | G | | | E | G | *** | | * |
| F22Y/K232G/R238H/A272G | Y | G | | | H | G | *** | *** | ** |
| F22Y/K232G/R235G/R238E/ | Y | G | | G | E | G | *** | | * |

TABLE 2-continued

F22Y/A272G Mutants

| Mutant | F22 | K 232 | S 233 | R 235 | R 238 | A 272 | Amount of Protein in Active Band | NADPH Activity | NADH Activity |
|---|---|---|---|---|---|---|---|---|---|
| A272G | | | | | | | | | |
| F22Y/K232G/ R235G/R238H/ A272G | Y | G | | G | H | G | *** | * | * |
| F22Y/K232G/ R235T/R238H/ A272G | Y | G | | T | H | G | *** | ** | * |
| F22Y/S233T/ R235S/R238H/ A272G | Y | | T | S | H | G | *** | *** | * |

NYD = NOT YET DETERMINED

Other mutants were prepared at residues which are not known to interact directly with the cofactor but which are between or adjacent to the region of K232 through R238 such as F230, R236 and E237. Table 3 shows results from native gel assays with these mutants.

TABLE 3

Other mutants

| Mutant | F230 | R236 | E237 | Amount of Protein in Active Band | NADPH Activity | NADH Activity |
|---|---|---|---|---|---|---|
| F230I | I | | | ** | *** | |
| F230L | L | | | *** | *** | |
| R236D | | D | | NM | NM | NM |
| R236E | | E | | NM | NM | NM |
| R236N | | N | | NM | NM | NM |
| R236S | | S | | NM | NM | NM |
| R236Y | | Y | | NM | NM | NM |
| E237R | | | R | NM | NM | NM |
| E237S | | | S | * | * | |

NM = NOT MEASURABLE DUE TO LOW INTRACELLULAR PROTEIN LEVELS

Combinatorial mutagenesis can also be used to produce cassettes wherein random mutations are made at almost every residue at a selected site. Combinatorial mutagenesis will yield every combination of mutants. For three sites, i.e. K232, R235 and R238, this will yield 203 possible combinations. Accordingly, mutants produced by combinatorial mutagenesis will be screened initially through a more rapid screening assay. There are several approaches to developing a rapid screening assay for identifying positive mutants. While the simplest method would be to screen for increased NADH-dependent activity in the individual cell clones, this may be difficult as *E. coli* naturally expresses several enzymes that utilize the cofactor and 2,5-diketo-D-gluconic acid substrate and this may mask the activity of the mutant enzymes in an assay. Accordingly, an alternative approach is to express the mutant away from the contaminating enzymes, i.e. as a fusion protein which is secreted into the periplasm or culture medium. For this assay a vector such as peZZ, which contains two copies of a synthetic IgG binding domain, or "Z" domain, that was derived from staphylococcal protein A, can be used. peZZ has been used previously to secrete various proteins into the culture media of *E. coli* fermentations (Moks et al. Bio/tech 1987 5:379–382). The IgG binding domain allows for rapid affinity purification (Moks et al. Bio/tech 1987 5:379–382). Accordingly, in this method the 2,5-diketo-D-gluconic acid reductase containing a randomized cassette is inserted into the peZZ vector (or another vector capable of secretion of the recombinant gene product from the host cell) and transformed into the host cell. The host cells are then grown up in the presence of an appropriate antibiotic to eliminate untransformed cells. The cells are then diluted, and spread out onto agar plates containing the appropriate antibiotic. Once colonies have formed, they can be picked and placed in the wells of a 96-well microtiter plate containing media and the appropriate antibiotic and incubated overnight. After the cultures have grown, a sample of the contents of the wells can be stamped out onto new agar plates onto which nitrocellulose filters have been placed. After the new colonies have formed, the filters can be removed and placed onto 3 MA paper that has been soaked in NADH and 2,5-diketo-D-gluconic acid. The nitrocellulose can then be removed and the 3 MM paper can be observed under ultraviolet light. Colonies that cause a dark spot to appear on the paper can then be chosen for further characterization including DNA sequencing of the mutant 2,5-diketo-D-gluconic acid reductase gene in the expression plasmid.

Another rapid screening method comprises phage display wherein mutant reductases are expressed on the surface of phage particles, and either selected on an immobilized NADH column or screened in microtiter plates in a manner similar to that described above for the fusion protein assay.

Eight single mutants with apparent NADH activity, as well as the wild type enzyme, were expressed in one liter cultures and purified by two ion exchange steps and one gel filtration step. The activities of the purified enzymes were assayed in 96-well microtiter plates on a plate reader. Both the substrate concentration and the NADH concentration were varied, and data were used to fit the following rate equation (1) for an ordered bi bi mechanism in the absence of products.

Equation (1) is:

$$\frac{dP}{dt} = \frac{E_t k A B}{K_{ia} K_b + K_b A + K_a B + AB} \quad (1)$$

wherein:
A = NADH concentration;
B = 2,5-diketo-D-gluconic acid concentration;
$K_a$ = Michaelis Constant for NADH;

$K_b$=Michaelis Constant for 2,5-diketo-D-gluconic acid;
$K_{ia}$=Dissociation Constant for NADH;
k=$k_{cat}$ for activity with NADH; and
$E_t$=Total enzyme concentration.

However, the parameters could not be fit in this model with any accuracy, due to the large apparent value of $K_M$ for 2,5-diketo-D-gluconic acid, and the low concentration of 2,5-diketo-D-gluconic acid that was used. The 2,5-diketo-D-gluconic acid concentrations were not large enough to saturate the enzyme, so a further mathematical simplification was required. Preliminary fitting of the model indicated both $k_{cat}$ and $K_b$ to be very large in comparison to $K_a$ and $K_{ia}$. Therefore, the rate equation was simplified to the following equation (2):

$$\frac{dP}{dt} = \frac{E_t\left(\frac{k}{K_b}\right)AB}{K_{ia} + A} \quad (2)$$

This equation is only valid when B<<$K_b$.

This equation was then used to fit the kinetic data, with much better results. Parameters obtained by the best fits are provided in Table 4.

Other comparisons can also be made between the different mutants using these parameters. For example, when NADH is the varied substrate, the term $k_{cat}B/K_b$ becomes the apparent $k_{cat}$ and $K_{ia}$ becomes the apparent $K_a$. Therefore, the term $k_{cat}B/K_bK_{ia}$ becomes the $k_{cat}/K_a$ apparent, which is a well-accepted means for comparing the kinetic performance of the different mutants with the NADH cofactor. The values of this parameter can also be seen in Table 4.

The two mutations at Arg238 had varied effects. Like the mutations at Arg235, R238E increased the apparent $K_a$ more than 3-fold while it also doubled the apparent $k_{cat}$. In comparison, the R238H mutant had both a slightly lower apparent $K_a$ than the wild type and it had a more than 5-fold improvement in the apparent $k_{cat}$.

Most of the mutants that were identified to have activity with NADH also retained activity with NADPH. However, the R238E and R238D mutation both abolished NADPH-dependant activity, as assayed on the native gels. It has already been demonstrated in 3-αHSD from rat liver that the analogous arginine is required for pre-steady state kinetic transients to be observed. This kinetic transient was attributed to an anchoring of NADPH by the arginine. It is now apparent that a charge reversal at this site can not only destroy the anchoring effect with NADPH, but it can completely prevent catalytic activity with NADPH. However, the cofactor binding pocket is still intact, as seen by the existence of improved activity with NADH.

Several preferred mutants such as K232G/R238H, K232G/R235G/R238H, and K232G/R235G/R238E can be completely purified and subjected to an in vivo modeling process to assess the performance of these mutant enzymes in industrial production of vitamin C. A purification method for mutants which does not rely on a dye affinity step is outlined in Example 3. The first step in this modeling process is to obtain rate equation parameters. This is accomplished by first examining initial rates in the absence of products, for each cofactor, and then fitting the results to the Michaelis-Menten equation through hyperbolic regression. These values can also be obtained by double reciprocal or Lineweaver-Burk plots, as the slopes and intercepts of the best fit lines to the reciprocals. The values from the hyper-

TABLE 4

Kinetic parameters with NADH of selected cofactor binding site residue mutants

| Mutant | $k_{cat}/K_b$ min$^{-1}$/mm$^{-1}$ | $K_{ia}$ (mM) | $(k_{cat}/K_b)/(k_{cat}/K_b)_{wt}$ | $K_{ia}/(K_{ia})_{wt}$ | $(k_{cat}/K_bK_{ia})/(k_{cat}/K_bK_{ia})_{wt}$ |
|---|---|---|---|---|---|
| wild type | 0.724 ± 0.026 | 2.6 ± 0.16 | 1.00 | 1.00 | 1.00 |
| K232G | 0.874 ± 0.028 | 2.02 ± 0.12 | 1.21 | 0.78 | 1.55 |
| K232M | 0.593 ± 0.023 | 3.89 ± 0.23 | 0.82 | 1.50 | 0.55 |
| K232Q | 0.634 ± 0.037 | 3.87 ± 0.34 | 0.88 | 1.49 | 0.59 |
| K232S | 0.318 ± 0.018 | 2.82 ± 0.27 | 0.44 | 1.08 | 0.40 |
| R235G | 3.58 ± 0.023 | 8.42 ± 0.69 | 4.94 | 3.24 | 1.53 |
| R235T | 1.34 ± 0.28 | 8.84 ± 2.28 | 1.85 | 3.40 | 0.54 |
| R238E | 1.49 ± 0.24 | 8.45 ± 1.74 | 2.06 | 3.25 | 0.63 |
| R238H | 3.87 ± 0.13 | 2.07 ± 0.13 | 5.35 | 0.80 | 6.71 |

As can be seen from data in Table 4, some of the mutants identified as having improved activity with NADH on the native gel actually had activity no better than wild type with NADH.

They may have been identified due to increased expression levels as compared to wild type. K232Q, K232M and K232S all have an apparent $k_{cat}$ below that found with wild type and an apparent $K_a$ that is higher than wild type. The mutant at Lys232 that demonstrated the greatest improvement in cofactor dependency as compared to wild type is K232G mutant. This mutant has both a slightly higher apparent $k_{cat}$, and a lower apparent $K_a$, as compared to the wild type.

The two mutations at Arg235 both increased the apparent $k_{cat}$ and the apparent $K_a$. Both mutations increased the apparent $K_a$ more than 3-fold. The R235T mutation increased the apparent $k_{cat}$ 2-fold, while the R235G mutant increased it 5-fold.

bolic regression analysis can then be used to calculate the slopes and intercepts of the best fit lines to the data. The slopes and intercepts can then be replotted versus the inverse of the substrate concentrations in order to get steady state rate equation parameters (Cleland, W. W. (1970) "Steady State Kinetics", The Enzymes: Kinetics and Mechanism. Ed. P.D. Boyer, Academic Press: NY, N.Y.). Initial estimates were completed for both NADH and NADPH for the K232G/R238H mutant.

The new slopes and intercepts are then used to obtain the parameters in the following rate equation (3) which was specifically derived for this modeling process for an enzyme using both NADH and NADPH, in the absence of product:

$$\frac{d[P]}{dt} = \frac{E_t \begin{pmatrix} K_{ia}^y K_b^y V^x [NADH][S] + K_a^y V^x [NADH][S]^2 + \\ K_{ia}^x K_b^x V^y [NADPH][S] + K_a^x V^y [NADPH][S]^2 \end{pmatrix}}{\begin{pmatrix} K_{ia}^x K_{ia}^y K_b^x K_b^y + K_a^x K_a^y [S]^2 + K_a^y [S]^2 [NADH] + \\ K_a^x [S]^2 [NADPH] + K_{ia}^x K_b^x K_a^y [S] + K_{ia}^y K_b^y K_a^x [S] + \\ K_b^x K_b^y (K_{ia}^y [NADH] + K_{ia}^x [NADPH]) + \\ (K_{ia}^y K_b^y + K_b^x K_a^y)[NADH][S] + \\ (K_{ia}^x K_b^x + K_b^y K_a^x)[NADPH][S] \end{pmatrix}} \quad (3)$$

wherein:
   superscript x=kinetic parameter for NADH only;
   superscript y=kinetic parameter for NADPH only;
   S=substrate concentration (2,5-diketo-D-gluconic acid);
   $E_t$=total enzyme concentration;
   $K_a$=Michaelis constant for cofactor;
   $K_b$=Michaelis constant for substrate;
   $K_{ia}$=dissociation constant for cofactor;
   V=$k_{cat}$, or turnover number, for activity with each cofactor;
   t=time; and
   P=product concentration (2-keto-L-gulonic acid)

The following table shows estimates of rate equation parameters determined using equation (3) for mutant K232G/R238H based upon one data set in the absence of product.

|          | NADPH        | NADH         |
|----------|--------------|--------------|
| $K_a$    | 0.267 mM     | 0.357 mM     |
| $K_b$    | 87.7 mM      | 71.5 mM      |
| $K_{ia}$ | 0.00532 mM   | 0.472 mM     |
| V        | 333 min$^{-1}$ | 357 min$^{-1}$ |

The main difference between the kinetic parameters with the two cofactors appears to be the difference in $K_{ia}$ which is the dissociation constant of the cofactor and is equal to the ratio of $k_2/k_1$, wherein $k_2$ is the off rate of the reduced cofactor and $k_1$ is the on rate of the reduced cofactor. This is believed to be due to a difference in the mode of binding, possibly attributable to an anchoring of the phosphate of NADPH by His238. Still, the $K_{ia}$ for NADH of this mutant is 5 times better than the $K_{ia}$ for the wild type (shown in Table 4).

The results of the initial rate equation can be used to estimate the performance of the mutant enzyme in vivo. Estimated total cofactor concentration in an *E. coli* cell is about 1.7 mM, with 77%. of that as NAD(H) (Lundquist, R. and Olivera, B. M. J. Bio. Chem. 1971 246:1107–1116). Mutant enzymes with activity predicted to be superior to wild type 2,5-diketo-D-gluconic acid reductase can thus be identified.

Accordingly, in addition to methods of producing enzymes with altered cofactor dependency, the present invention also relates to specific mutants of 2,5-diketo-D-gluconic acid reductase A enzyme which catalyze the conversion of 2,5-diketo-D-gluconic acid to 2-keto-L-gulonic acid by use of cofactor NADH, altered amounts of NADPH or a combination of NADH and NADPH. These mutants were prepared by identifying a cofactor specificity site in the wild type 2,5-diketo-D-gluconic acid reductase A enzyme and modifying one or more amino acid residues within the cofactor specificity site. In a preferred embodiment of the present invention, the mutant 2,5-diketo-D-gluconic acid reductase enzyme comprises a mutation at residue 238 alone, or in combination with one or more mutations at residues 230 through 237. Examples of preferred mutants of the present invention include, but are not limited to, those mutated at residues 238, 232 and 238, 235 and 238, and 232, 235 and 238 such as R238E, R238H, K232G/R238H, K232S/R238H, K232G/R235G/R238E and K232G/R235G/R238H. Other preferred mutants include those prepared by homology to other enzymes in the aldo-keto reductase superfamily with specificity for NADH such as K232R/V234F/R235N/R238H, V234Y/R235D/R238H and S233T/R235S/R238H. As will be obvious to those of skill in the art upon this disclosure, mutants of other 2,5-diketo-D-gluconic acid reductase enzymes such as 2,5-diketo-D-gluconic acid reductase B can be prepared in a similar manner through identifying a cofactor specificity site via sequence alignment with 2,5-diketo-D-gluconic acid reductase A.

Also provided in the present invention are DNA sequences encoding these mutants and vectors and host cells for expression thereof. A number of promotion/control systems and suitable prokaryotic hosts are available for use in the present invention. Similar prokaryotic hosts can be used for both cloning and expression. Examples of appropriate host cells for cloning include, but are not limited to, *E. coli* XL1-Blue, *E. coli* RV308, *E. coli* MM294, *E. coli* K12 strain (ATCC No. 31446), *E. coli* B, *E. coli* X1776 (ATCC No. 31537) and *E. coli* DH-1 (ATCC No. 33489) with *E. coli* XL1-Blue being preferred. For expression, these strains as well as *E. coli* JM109, *E. coli* Top 10, *E. coli* W3110 (F-, λ, prototrophic ATCC No. 27325) bacilli such as *Bacillus subtilus*, and other enterobacteriaceae such as *Salmonella typhimurium* or *Serratia marcesans* and various Pseudomonas species may be used, with *E. coli* JM109 being preferred. Particularly preferred hosts are those capable of converting glucose and other commonly available metabolites to 2,5-diketo-D-gluconic acid. Examples of such hosts are generally found among the genera Acetobacter, Gluconobacter, Acetomonas, and Erwinia. Specific examples of such hosts include, but are not limited to, Erwinia herbicola ATCC No. 21998 (also considered an *Acetomonas albosesamae* in U.S. Pat. No. 3,998,697); Acetobacter (Gluconobacter) oxydans subspecies melanozenes, IFO 3292, 3293 ATCC No. 9937; Acetobacter (Gluconobacter) cerinus IFO 3263 IFO 3266; *Gluconobacter rubiginous*, IFO 3244; *Acetobacter fragum* ATCC No. 21409; Acetobacter (Acetomonas) suboxydans subspecies industrious ATCC No. 23776; Pantoea or *Erwinia citrea*, ATCC31623; and *Pantoea agglomerans* (also known as *Erwinia herbicola*), ATCC 43348.

It is preferred that plasmid expression or cloning vectors or conjugative plasmids containing replication and control sequences that are derived from species compatible with the host cell be used in connection with these hosts. Vectors typically carry a replication origin as well as marker genes that are capable of providing phenotypic selection in transformed cells. For example, *E. coli* is typically transformed using pBR322, a plasmid derived from an *E. coli* strain. pBR322 contains genes for ampicillin and tetracycline resistance and thus provides an easy means for identifying transformed cells. For expression, the pBR322 plasmid is also modified to contain promoters used by the microbial organism for expression of its proteins. Promoters used commonly in recombinant expression in microbial organisms include the β-lactamase (penicillinase) and lactose promoter systems and the tryptophan operon promoter system. However, other microbial promoters can also be used.

DNA sequences encoding 2,5-diketo-D-gluconic acid reductase enzymes or mutants thereof are included in these vectors via suitable cleavage and ligation. Unnecessary or inhibitory sequences can be deleted. The recombinant prokaryotic enzyme can be expressed and purified. Permeabilized or broken cells can be used directly as catalysts. Alternatively, host cells can be selected so that once transformed they are capable of effecting the entire conversion of glucose or other suitable metabolite to the desired 2-keto-L-gulonic acid product. Host cells transformed with the wild type or mutant plasmid DNA are then cultured under conditions favoring enzyme expression.

The new mutant enzymes can be used in metabolically engineered organisms to produce 2-keto-L-gulonic acid from glucose in a single fermentation step in similar fashion to procedures described by Anderson et al. for the wild type enzyme (Science 1985 230:144–149). However, flexibility in catalyzing the enzymatic reaction via the mutants of the present invention with NADH or nonspecifically with NADH or NADPH provides advantages. For example, the intracellular NAD(H) pool is believed to be approximately 3 to 5 times larger than the available NADP(H) pool. Thus, these enzymes are expected to function more efficiently in in vivo processes as cofactor concentrations will not be as limiting. Further, since the cost of NADPH is an order of magnitude greater than that of NADH, use of the mutants of the present invention in any in vitro system wherein cofactor must be purchased and provided for the enzymes provides a significant cost saving advantage. Further, as shown in Tables 1 through 4, several of the mutant enzymes exhibit increased levels of apparent expression, which could lead to an increased rate of production of 2-keto-L-gulonic acid.

The following nonlimiting examples are provided to further illustrate the present invention.

EXAMPLES

Example 1

Summary of New Restriction Sites in pATP003.xb used in Cassette Mutagenesis

Xho I cuts at C$^{\triangledown}$TCGAG. Therefore, the existing Xho I site in the reductase gene was eliminated by a single silent mutation from:

```
            144      _Xho I_     149
    . . . CCG CAC CTC GAG CGC ATC . . . (SEQ ID NO:2)
           P   H   L   E   R   I  (SEQ ID NO:3)
to:
            144                  149
    . . . CCG CAC CTC GAA CGC ATC . . . (SEQ ID NO:4)
           P   H   L   E   R   I  (SEQ ID NO:3)
```

A Xho I site was then introduced downstream of the region of interest by a similar single silent mutation from:

```
          237                    242
    . . . GAG CGC CTC GAA GAG AAC . . . (SEQ ID NO:5)
           E   R   L   E   E   N  (SEQ ID NO:6)
to:
          237      _Xho I_       242
    . . . GAG CGC CTC GAG GAG AAC . . . (SEQ ID NO:7)
           E   R   L   E   E   N  (SEQ ID NO:6)
```

Bsu36 I cuts at CC$^{\triangledown}$TNAGG. A unique Bsu36 I site was introduced upstream of the region of interest with three silent mutations from:

```
          216                            222
    . . . CAG GCC GTG CTC CGT TGG CAC . . . (SEQ ID NO:8)
           Q   A   V   L   R   W   H  (SEQ ID NO:9)
to:
          216          _Bsu36 I_        222
    . . . CAG GCC GTC CTC AGG TGG CAC . . . (SEQ ID NO:10)
           Q   A   V   L   R   W   H  (SEQ ID NO:9)
```

Through introduction of these new restriction sites it is possible to remove a 57 base pair fragment from the pATP003.xb vector with double digestion of Bsu36 I and Xho I.

Example 2

Native Gel Assay

The native gel assay was performed in accordance with a procedure similar to that described by Seymour, J. L. and Lazarus, R. A. (Anal. Biochem. 1989 178:243–247) with some modifications. For this assay, 50 ml cultures of LB media containing Ampicillin (0.1 g/L) were inoculated with 0.5 ml of a saturated overnight culture of E. coli strain JM109 harboring the pATP003.xb plasmid containing the mutant oligonucleotide cassettes. The cultures were grown until the absorbance of the culture at 600 nm was approximately equal to 1.0. The cultures were then induced by adding IPTG to a final concentration of 1 mM. The cultures were allowed to grow another 4 hours at 37° C. The cells were harvested by centrifugation and the cell pellets were temporarily frozen. The pellets were then thawed on a later day and the cells were lysed with the Bug Buster detergent (Novagen) containing Complete Protease Inhibitor Cocktail Tablets (Roche) in accordance with the manufacturers' directions. After 10 minutes in the presence of the detergent, the cell debris was removed by centrifugation, and the supernatant was mixed with a loading dye and then loaded directly onto two identical polyacrylamide gels without SDS. The gels were run in a cold room at no more than 3 Watts per gel. The native proteins migrate according to their charge-to-mass ratio. This separates out the different enzymes and moves the recombinant reductase away from naturally occurring enzymes that have activity with these substrates. When the loading dye reached the bottom of the gel, the gels were removed and washed in water. The two gels were then soaked in a 1 mM solution of cofactor and 50 mM bis-Tris buffer, pH 7.0. One gel was soaked in NADH and the other in NADPH. After 15 minutes, the gels were rinsed off and overlaid with a piece of Whatman filter paper that had been soaked in a solution of 20 mM 2,5-diketo-D-gluconic acid and 50 mM bis-Tris, pH 7.0. Both reduced cofactors fluoresce in the ultraviolet range, while the oxidized cofactors do not. Accordingly, at various times the gels were placed on an ultraviolet transilluminator. Regions of the gel where there is enzymatic activity exhibit attenuated fluorescence. They show up as dark bands when viewed under ultraviolet light. The gels were usually observed after 10 minutes of contact with the filter paper in order to observe any mutants with very high activity. In some cases, the gels were then allowed to sit under the filter paper for up to 2 hours in order to detect less active mutants. The two gels were then photographed and compared to provide an indication of the activity of the mutants with each cofactor. Expression levels of the mutants were estimated by Coomassie staining of the gels as well.

Example 3

A purification protocol which does not require dye-affinity chromatography

Cells containing plasmids for some of the mutant reductases were grown up on a 1 liter scale using a 10 ml inoculum from a saturated overnight culture. The cells were grown until absorbance of the culture at 600 nm was approximately 1.0. The cells were then induced by adding IPTG to a final concentration of 1 mM. The cells were harvested after growth at 37° C. for 4 hours. The cells were then pelleted by centrifugation and frozen for later use. At a later date, cells were thawed and lysed with the Bug Buster detergent (Novagen) containing Complete Protease Inhibitor Cocktail Tablets (Roche). The pH was lowered to 5.5 with 20 mM sodium acetate (NaOAc) and NaCl was added to a final concentration of 0.15 M. After 10 minutes with the detergent, the cell debris was removed by centrifugation, and the supernatant was loaded onto disposable chromatography columns containing a 10 ml bed volume of DEAE Cellulose (Sigma) for a batch weak ion exchange step. The resin was washed with 0.15 M NaCl, still in the presence of NaOAc, pH 5.5. The bound proteins were then eluted by two washes with 0.5 M NaCl. The eluted material was then diluted back to 0.15 M NaCl by the addition of more 20 mM NaOAc buffer. This was then loaded onto a 4.6 mmD/100mml PEEK column (PerSeptive Biosystems) containing 50 μm DEAE Ceramic HyperD F resin (BioSepra) using an FPLC system. The high performance resin was washed with 0.1 M NaCl and the bound proteins were eluted using a linear salt gradient up to 0.4 M NaCl. Active fractions were pooled and the pH was raised to 7.0 using 50 mM bis-Tris. The pooled fractions were then concentrated by ultrafiltration in a stirred cell unit using a polyethersulfone membrane with a 10,000 MW cut-off (Millipore). The concentrate was loaded onto a Superdex-75 gel filtration column (Pharmacia) using 50 mM bis-Tris pH 7.0 with an FPLC system. The active fractions were again pooled. A small sample from the pooled fractions was electrophoresed on a polyacrylamide gel in the presence of SDS in order to insure homogeneity of the final product. The final product was aliquoted and frozen for later use in the determination of the kinetic characteristics of the NADH active mutants.

Example 4

Kinetic Determinations

NADPH and NADH were prepared fresh for each use in kinetic measurements. These reactions were performed in 96-well microtiter plates using a SpectraMax 190 plate reader (Molecular Devices). Varying amounts of cofactor and substrate were added to the wells and reaction was initiated by the addition of the mutant enzyme. The final volume of each reaction was 200 μl, the reactions were buffered with 50 mM bis-Tris pH 7.0, and the temperature was held at 25° C. The course of the reaction was followed at 340 nm for NADPH and 375 nm for NADH. Initial rate data was collected in each well, and a standard curve was generated each day in order to correlate the change in absorbance of the reaction to a change in concentration of cofactors. All measurements were performed in triplicate (at least) and the runs were averaged for use in kinetic modeling.

What is claimed is:

1. A mutant of the wild type 2,5-diketo-D-gluconic acid reductase of SEQ ID NO:1 catalyzing conversion of 2,5-diketo-D-gulonic acid to 2-keto-L-gluconic acid and exhibiting increased activity with NADH, different activity with NADPH or NADH as compared to the wild type enzyme, or activity with both NADPH and NADH.

2. A mutant of 2,5-diketo-D-gluconic acid reductase of SEQ ID NO:1 wherein an amino acid at residue 238 alone or at residue 238 and one or more of residues 230 through 237 are mutated.

3. A DNA encoding the mutant 2,5-diketo-D-gluconic acid reductase enzyme of claim 1.

4. A vector comprising the DNA of claim 3.

5. A host cell comprising the vector of claim 4.

* * * * *